United States Patent [19]

Watt

[11] 3,986,507

[45] Oct. 19, 1976

[54] PARENTERAL CONTAINER

[75] Inventor: W. E. R. Watt, Barto, Pa.

[73] Assignee: Inpaco, Coplay, Pa.

[22] Filed: Apr. 16, 1975

[21] Appl. No.: 568,572

[52] U.S. Cl. .............................. 128/214 D; 128/272
[51] Int. Cl.[2] .............................................. A61M 5/00
[58] Field of Search ......................... 128/214 D, 272

[56] References Cited

UNITED STATES PATENTS

| | | | |
|---|---|---|---|
| 3,509,879 | 5/1970 | Batish et al. | 128/272 |
| 3,519,158 | 7/1970 | Anderson | 128/272 |
| 3,788,374 | 1/1974 | Saijo | 128/272 |

*Primary Examiner*—Louis G. Mancene
*Assistant Examiner*—Robert F. Cutting
*Attorney, Agent, or Firm*—Sherman Levy

[57] ABSTRACT

A parenteral container such as a blood bag is provided that has a construction that is compatible with materials such as red blood cells and which, when used as a blood bag, results in a low degree of hemolysis during the storage of the red blood cells. The bag is sealed on its sides and is provided with grommets for hanging. A polyolifin fitment is secured on the bag, and the fitment has two ports for use as an administration set port and an outlet port. The joint of the inlet port to the PVC tubing is an important feature of the present invention.

8 Claims, 5 Drawing Figures

FIG. 1.
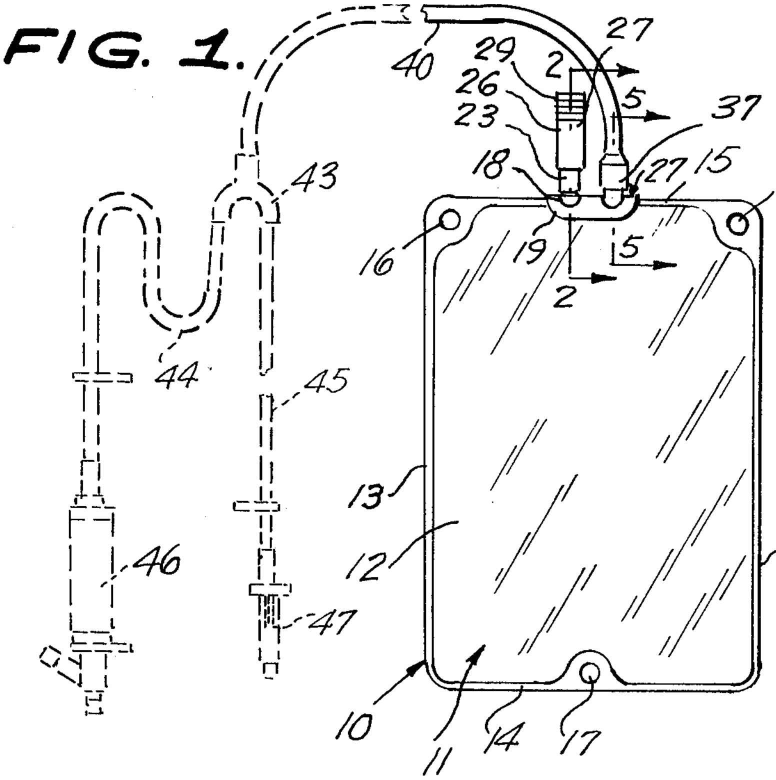
FIG. 3.
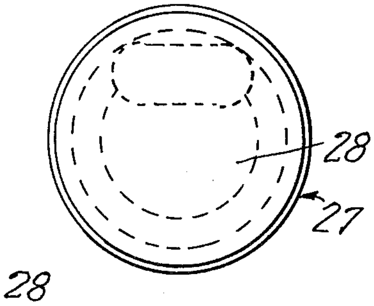
FIG. 2.
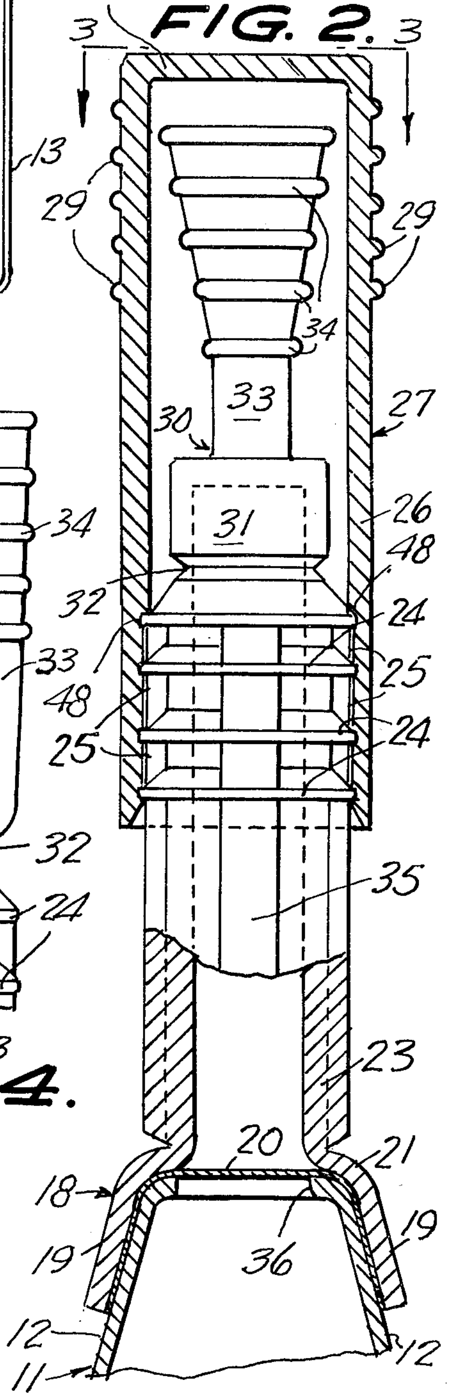
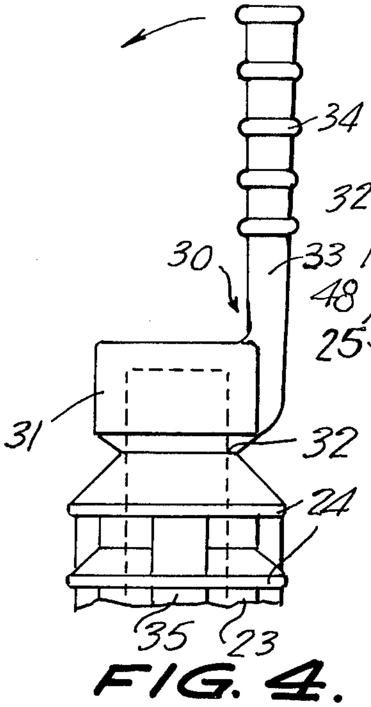
FIG. 4.
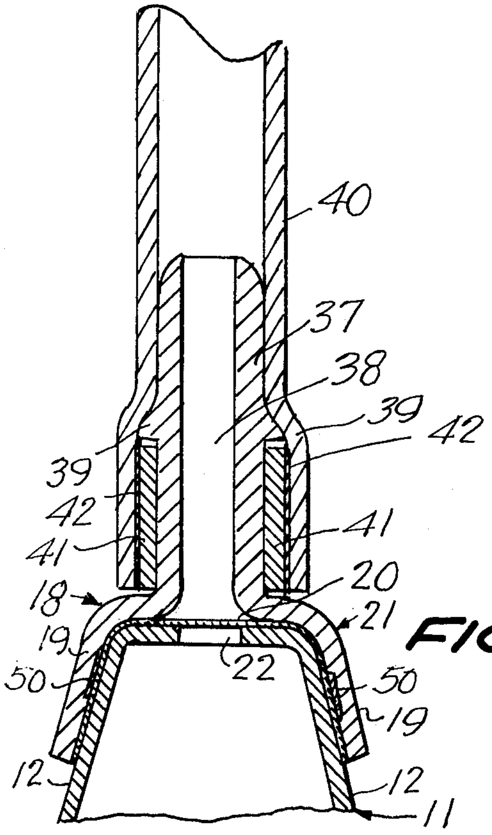
FIG. 5.

PARENTERAL CONTAINER

BACKGROUND OF THE INVENTION

Field of the Invention

The present invention relates to a parenteral container such as a blood bag and more particularly to blood bags wherein whole blood is centrifuged to pack the red blood cells. The packed red blood cells are then mixed with glycerine in the bag through the administration set and are shaken until they are in equilibrium. In this form the red blood cells can be held for a considerable period of time. When the red blood cells are to be used, the bag is thawed, the glycerin washed out in a suitable mechanism, and the red blood cells are then infused.

SUMMARY OF THE INVENTION

A parenteral bag such as a blood bag is provided wherein the bag is made of a polyolifin resin that is compatible with red blood cells, and wherein the bag is sealed on its sides and provided with grommets that are suitably placed for hanging. A polyolifin fitment is sealed on the bag, and the fitment has two ports--namely, an administration set port and an outlet port. In accordance with the present invention, the joint of the inlet port to the PVC tubing is provided in an advantageous manner. There is further provided other important features such as a special rip-off closure that has a vertical tear-off tab, and the positioning of the tear-off tab facilitates easy molding and ring sealing.

The primary object of the present invention is to provide a parenteral container such as a blood bag that has improved characteristics and advantages for handling red blood cells as compared to previous blood bags.

Still another object of the present invention is to provide a parenteral bag that is ruggedly constructed and efficient and which is relatively simple and inexpensive to manufacture.

Other objects and advantages of the present invention will become apparent in the following specification when considered in the light of the attached drawings.

BRIEF DESCRIPTION OF THE DRAWINGS

FIG. 1 is an elevational view of the parenteral container constructed in accordance with the present invention.

FIG. 2 is an enlarged sectional view taken on the line 2—2 of FIG. 1.

FIG. 3 is a plan view taken generally on the line 3—3 of FIG. 2.

FIG. 4 is a view taken at right angles to the view shown in FIG. 2 and illustrating the rip-off cap.

FIG. 5 is an enlarged sectional view taken on the line 5—5 of FIG. 1.

DESCRIPTION OF THE PREFERRED EMBODIMENT

Referring in detail to the drawings, the numeral 10 indicates the parenteral container of the present invention that comprises a bag 11 made of a flexible material such as a flexible plastic material, and the bag 11 embodies portions 12 that have their side edges suitably secured together or formed integral as at 13. Likewise, the bottom and top edges 14 and 15 of the bag 11 are of integral construction as shown in FIG. 1. The numeral 16 indicates grommets formed in the upper corner portions of the bag 11, and a similar grommet 17 is provided in the lower intermediate portion of the bag.

As shown in the drawings, a fitment 18 is mounted on the upper intermediate portion of the bag 11. The fitment 18 includes a base portion 21 that includes spaced apart side portions 19, FIG. 5. The numeral 20 indicates a section of film that can be punctured or ruptured in selectively exposed opening 22 in the bag 11.

As shown in FIG. 2, a fitting 23 extends from the fitment 18 and is secured thereto or formed integral therewith, and the fitting 23 includes a stepped portion or sealing rings 24 that are adapted to be selectively co-act and engage interference surfaces 25 that are formed on the interior of a wall section 26 of a safety cap 27, FIG. 2. The safety cap 27 includes a top portion 28. Also, the outer surface of the cap 27 has knurled or roughened portions or surfaces 29 to facilitate the manual handling or gripping of the safety cap 27.

A rip-off cap 30 is provided on the upper or outer end of the fitting 23, and the rip-off cap 30 includes a portion 31 that is adapted to be separated along the line or junction 32 from the remaining portion of the fitting 23. The portion 31 has an upstanding tapered extension 33 that has knurled or roughened portions 34 thereon whereby the portion 33 can be gripped when the rip-off cap is to be removed along the line 32. A passageway 35 in the fitting 23 is adapted to selectively communicate with an opening 36 in the bag 11 when the film 20 is punctured or ruptured.

Referring to FIG. 5 of the drawings, numeral 37 indicates a nipple that is formed integral with or secured to the fitment 18, and the nipple 37 has a passageway or port 38 therein that can selectively communicate with the opening 22 when the adjacent portion or the film 20 is punctured. A shoulder 39 is arranged on the outer periphery of the nipple 37, FIG. 5, for co-action with the adjacent portion of a hollow flexible tube 40 to help retain the parts in their proper assembled position. The numeral 41 indicates tubing that is secured in place by a solvent weld 42. Tubes 44 and 45 are connected to the end of the tube 40 by means of a connection 43, and a conventional drip chamber 46 and stylii 47 are arranged as shown in FIG. 1. The drip chamber 46 and stylii 47 are conventional and form no part of the present invention.

From the foregoing, it will be seen that there has been provided a parenteral container, and in use with the parts arranged as shown in the drawings, the bag 11 is adapted to be made of a material that is compatible with red blood cells and wherein there will result in a low degree of hemolysis during the storage of the red blood cells. The bag is sealed on all its sides as indicated by the numerals 13, 14 and 15. The bag is provided with grommets such as the grommets 16 and 17 for convenience of hanging. The polyolifin fitment 18 is secured on the bag, and the fitment has two ports for use as an administration set port and an outlet port.

The fitting 23 has a rip-off cap or portion 30 that can be manually separated from the fitting 23 when the device is to be used. In addition, the safety cap 27 is mounted over the rip-off cap 30 as shown in FIG. 2 until the bag is to be used. With the parts in the position of FIG. 2, the sealing rings 24 co-act with the interference surfaces 25 on the interior of the safety cap 27.

As shown in FIG. 5, the tube 40 is fixed in place by means of the tongue or flange 39 as well as the tubing 41 which has a solvent weld 42 to the adjacent parts so that accidental separation of these members is prevented.

It is to be understood that the parts can be made of any suitable material and in different shapes and sizes as desired or required.

Certain of the parts can be heat sealed together or otherwise secured in place. The present invention can be used in conjunction with or on a form, fill machine such a form, fill, seal machine whether it is of the vertically disposed or horizontally disposed type. In FIG. 2 the numeral 48 indicates a cap stop. The cap stop is built into the cap. There is an actual interference between the cap and the fitment to provide a squeegie effect as indicated by the numerals 24 and 25. In FIG. 5, the numeral 50 indicates a seal area between the film and the fitment. A heat seal is also provided between the film and the fitment as shown in the drawings. Also, as shown in FIG. 5, the outside diameter of the tube port nipple 37 is larger than the inside diameter of the tubing. A solvent weld 42 is provided between the two pieces of tubing. A heat seal may be provided at the point 50 betwen the fitment base and the bag film. The squeegie configuration 24 and 25 prevents wet contamination of the rip-off cap area when the safety cap 27 is removed.

In use, whole blood is centrifuged to pack the red blood cells. The packed red blood cells are then mixed with glycerin in the bag through the administration set and are shaken until they Equilibriate. In this form the red blood cells can be held for up to ten years. When they are to be used, the bag is thawed, the glycerin washed out in a machine such as an IBM machine and the red blood cells are then infuged.

While various patents have been provided on parenteral containers, heretofore, the present invention possesses certain important differences and advantages not found in the prior patents. For example, the present invention has a piercable film with a heat sealed fitment or a rip-open fitment that is heat sealed to the bag structure. There is also provided a safety closure to help maintain the sterility of the area through which the piercing spike must come in contact. With the present invention, the fitments are not molded into the package in its initial form.

With further reference to FIG. 1, the structure in the broken lines and indicated by the numerals 46 and 47 is a standard commercial administration set. The present invention includes the PVC tube connected to the blood bag.

The bag is preferably a special polyolifin resin that is compatible with red blood cells and can be conveniently used by Red Cross personnel and the like so that it results in the lowest degree of hemolysis during the storage of the red blood cells. The bag is sealed on three sides with sealed in grommets placed for hanging, two at the top of the bag and one at the bottom center.

The polyolifin fitment on the bag is heat sealed. This fitment 18 has two ports, the administration set port and the outlet port. An important aspect of the present invention is the joint of the inlet port to the PVC tubing.

Generally, it is not believed that heretofore satisfactory ways of bonding polyethelene, other than thermo welding, sealing, joining and the like have been available. For example, there are no readily available adhesives and no way of bonding polyolifin to a material such as PVC. Thus, the task of making a satisfactory joint between the fitment inlet port and the PVC tubing has been solved by the addition of a second PVC segment 41 that is bonded by solvent to the inside of the PVC tube. This causes a mechanical interference type of bond between the PVC tube end and the polyolifin port. This joint may be made by first slipping a segment of tube over the inlet port past the interference ring.

Next, the PVC tube to be used is dipped in a solvent which softens the surface of the PVC tube and solvent welds it to the PVC segment already placed on the polyolifin inlet port. In addition to the joining of the PVC tube segment to the PVC tube, the solvent also helps to mold the PVC tube to the irregularities of the polyolifin inlet surface so as to effect a compact bond and make a good, tight, leak-free joint.

With further reference to the outlet port, the oulet port is of a length that prevents the stylii of an administration set from reaching the bag properly. Both the film areas under the outlet port and the inlet port are prepunched. The fitment is made so that this area is isolated and kept sterile by the rip-off closure 30.

When the frozen red blood cells are being thawed, in order to prevent contaminated water from entering into the outlet port, there has been provided the interference safety cap 27 and sealing points are provided to this cap. Also, the special rip-off closure or cap 30 has a vertical tear-off tab. The positioning of this tear-off tab facilitates easy mold and ring sealing. The sealing nest of the machinery will accept this whole port in a vertical position and a ring seal can be made between the film and the base of the fitment.

The fitment has been constructed to accept the standard styli. The film is punched out under both the fitment ports. The styli port, that is the one with the tear-off cap, has several features of importance. First, the position of the pull tab, the vertical and perpendicular arrangement to the sealing area, is important. Without this positioning, the fitment could not be placed in a sealing nest and a peripheral seal made around the base of that port.

Secondly, the styli port has wiper rings added to it so that with a safety cap placed on this port and the bag thawed in dirty water, upon removal this water is wiped back away from the opening area of the styli port, thus preventing contamination of this port prior to insertion of the styli. The safety cap is, of course, an addition and it prevents this area from becoming contaminated while immerged in the thawing water.

The container is adapted to be formed and the fitment attached on a form-fill-seal machine. The parenteral container can be made or used with devices such as that shown in prior U.S. patent applications Ser. No. 371,966 and U.S. Pat. No. 3,873,007, or similar metered product dispensing systems.

Although the invention has been illustrated and described with reference to the preferred embodiments thereof, we wish to have it understood that it is in no way limited to the details of such embodiments, but is capable of numerous modifications within the scope of the appended claims.

What is claimed is:

1. As a new article of manufacture, a parenteral container comprising a bag made of flexible material and said bag including portions that are sealed together at their sides, top and bottom edges, a fitment mounted on the upper intermediate portion of the bag and said fitment including a base portion, a fitting projecting from said fitment, a rip-off cap on said fitting, a safety cap removably mounted over said rip-off cap and fitting, a nipple spaced from said fitting and said fitting having an outwardly projecting tongue, a tubing having a portion thereof receiving said nipple and engaged by said tongue, and a tubing segment interposed between said tube and said nipple and secured thereto.

2. The structure as defined in claim 1 wherein said bag is made of polyolifin resin material that is compatible with red blood cells.

3. The structure as defined in claim 2 wherein a solvent provides a weld between the tubing and the tube.

4. The structure as defined in claim 3 and further including grommet means on said bag.

5. The structure as defined in claim 4 and further including squeegie means on said closure cap and said fitting.

6. The structure as defined in claim 5 wherein the container is formed and the fitment is attached on a form-fill-seal machine.

7. In a parenteral container, a bag of flexible material, a fitment on said bag, a fitting and nipple integral with said fitment, said nipple being spaced from said fitting and said fitting projecting outwardly from said fitment outwardly of said bag, a rip-off cap on said fitting, and a tube connected to said nipple, and a safety cap for selectively closing the fitting and rip-off cap, said fitting having sealing rings for coacting with interference surfaces on the interior of the safety cap.

8. The structure as defined in claim 7 and further including a tube mounted on said nipple, and a tubing segment interposed between the portion of the tubing and said nipple.

* * * * *